United States Patent
Ptchelinstev

(10) Patent No.: US 9,084,744 B1
(45) Date of Patent: *Jul. 21, 2015

(54) **USE OF *TILIACORA TRIANDRA* IN COSMETICS AND COMPOSITIONS THEREOF**

(75) Inventor: Dmitri S. Ptchelinstev, Jersey City, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/813,732

(22) Filed: Jun. 11, 2010

Related U.S. Application Data

(63) Continuation of application No. 12/345,707, filed on Dec. 30, 2008, now abandoned.

(51) Int. Cl.
*A61K 8/97* (2006.01)
*A61K 47/48* (2006.01)
*A61K 36/00* (2006.01)

(52) U.S. Cl.
CPC ........................................ *A61K 36/00* (2013.01)

(58) Field of Classification Search
IPC ..................................... A61K 8/97,47/48, 36/00
See application file for complete search history.

(56) References Cited

U.S. PATENT DOCUMENTS

| 4,322,438 A | 3/1982 | Peck |
| 5,310,554 A | 5/1994 | Haigh |
| 5,709,868 A | 1/1998 | Perricone |
| 6,146,640 A * | 11/2000 | Dyke ............................ 424/769 |
| 7,514,092 B2 | 4/2009 | Dryer et al. |
| 7,618,662 B2 | 11/2009 | Hines et al. |
| 8,771,758 B2 | 7/2014 | Ptchelintsev |
| 2002/0061339 A1* | 5/2002 | Stogniew et al. ............. 424/725 |
| 2003/0185933 A1* | 10/2003 | Ting et al. ........................ 426/11 |
| 2004/0126344 A1 | 7/2004 | Mahalingam et al. |
| 2006/0018867 A1 | 1/2006 | Kawasaki et al. |
| 2006/0134059 A1 | 6/2006 | Dryer et al. |

(Continued)

FOREIGN PATENT DOCUMENTS

| CN | 101559033 A | 10/2009 | |
| IN | 2002012411 | 11/2009 | |
| JP | 2005281284 | * 10/2005 | ............... A61K 7/48 |

OTHER PUBLICATIONS

American Academy of Dermatology. Sensitive Skin. Retrieved from the internet. <http://www.aad.org/media-resources/stats-and-facts/prevention-and-care/sensitive-skin>3 pages.*

(Continued)

*Primary Examiner* — Patricia A Leith
(74) *Attorney, Agent, or Firm* — David M. Joyal; Joan M. McGillycuddy

(57) ABSTRACT

The present disclosure relates to compositions and methods for treating, preventing and improving the condition and aesthetic appearance of skin, particularly, treating, preventing, ameliorating, reducing and/or eliminating fine lines and/or wrinkles of skin, where the compositions include natural plant constituents which increase expression levels genes, collagen replacement and retention, and cell proliferation of epidermis and dermis associated with the dermatological signs of aging. The compositions of the invention are topically applied to the skin, or are delivered by directed means to a site in need thereof, once daily in an amount effective in improving the condition and aesthetic appearance of skin.

5 Claims, 4 Drawing Sheets

A.

B.

(56) References Cited

U.S. PATENT DOCUMENTS

| | | | |
|---|---|---|---|
| 2007/0122492 A1 | 5/2007 | Behr et al. |
| 2007/0148106 A1 | 6/2007 | Wertz et al. |
| 2007/0161625 A1 | 7/2007 | Brown et al. |
| 2008/0206290 A1 | 8/2008 | Schulz et al. |
| 2008/0274453 A1 | 11/2008 | Hageman |
| 2009/0012273 A1 | 1/2009 | Nakamura et al. |
| 2009/0082252 A1 | 3/2009 | Ptchelintsev |
| 2009/0104291 A1 | 4/2009 | Kanazawa |
| 2010/0055210 A1 | 3/2010 | Lee et al. |
| 2010/0166677 A1 | 7/2010 | Ptchelintsev |
| 2010/0183528 A1 | 7/2010 | Maloney et al. |
| 2011/0081333 A1 | 4/2011 | Shantha et al. |
| 2012/0003331 A1 | 1/2012 | Ptchelintsev |
| 2012/0003332 A1 | 1/2012 | Zheng et al. |
| 2012/0225092 A1 | 9/2012 | Paufique |
| 2013/0149268 A1 | 6/2013 | Chen et al. |

OTHER PUBLICATIONS

Ricciarelli et al. Age-Dependent Increase of Collagenase Expression Can be Reduced by Alpha-Tocopherol via Protein Kinase C Inhibition. Free Radical Biology & Medicine. vol. 27, Nos. 7/8, pp. 7929-7937.*

Pieroni. Eating and Healing. Psychology Press. Mar. 7, 2005. p. 88.*

Sireeratawong et al. Acute and Subchronic Toxicity Study of the Water Extract from *Tiliacora triandra* (Colebr.) Diels in Rats; Songklanakarin J. Sci. Technol. 30 (5), 611-619, Sep.-Oct. 2008.*

Somnasang, P.R. Indigenous Food Use: Gender Issues in Rural Northeast Thailand . (Doctoral Dissertation) Retrieved from ProQuest Dissertations and Theses UMI No. 9706763, 1996, pp. 185, 192, 206 and 263.*

Healthy-skincare.com. Retrieved from the internet. <http://www.healthy-skincare.com/benefits-of-vitamin-e.html>. Retrieved on Aug. 24, 2011. 3 pages.*

American Academy of Dermatology. Sensitive Skin. Retrieved from the internet. <http://www.aad.org/media-resources/statsand-facts/prevention-and-care/sensitive-skin>. 3 pages, accessed Aug. 30, 2011.*

Ricciarelli et al. Age-Dependent Increase of Collagenase Expression Can be Reduced by Alpha-Tocopherol via Protein Kinase C Inhibition. Free Radical Biology & Medicine. (1999) vol. 27, Nos. 7/8, pp. 7929-7937.*

Pachaly et al. New Bisbenzylisoquinoline Alkaloids from *Tiliacora triandra*. Planta Medica. Oct. 1988; 54 (5). Abstract.*

Phadungkit. "Cosmeceuticals from Traditional Plants". Proceedings of the 34th Congress on Science and Technology of Thailand, Invited Speakers No. 35, Nov. 2, 2008 <URL:http://www.scisoc.or.th/stt/34/invited/35.pdf> abstract.

Sireeratawong et al. "Acute and subchronic toxicity study of the water extract from *Tiliacora triandra* (Colebr.) Diels in rats". Songklanakarin J. Sci. Technol. Sep.-Oct. 2008, vol. 30, No. 5, pp. 611-619, entire document, esp: abstract, p. 611 1st para, p. 612, 1st & 2nd para.

Pachaly et al. "New bisbenzylisoquinoline alkaloids from *Tiliacora triandra*". Planta Med. Oct. 1988; 54(5): 433-7. Planta Med 1988: 54(5):433-437. abstract.

Pavanand et al., Antimalarial Activity of *Tiliacora triandra* Diels against *Plasmodium falciparum* in vitro, Phytotheraphy Research., vol. 3, 215-217 (Oct. 1989).

Phadungkit. "Phytochemical Screening, Flavonoid Ceontent and Antioxidant Activity of *Tiliacora triandra* Leaf Extracts". 2nd Annual International Conference of Northeast Pharmacy Research 2010, Feb. 13-14, 2010.

Singthong et al. Extraction and physicochemical characterisation of polysaccharide gum form Yanang (*Tiliacora triandra*) leaves. Food Chemistry, Elsevier Ltd. NL, vol. 114, No. 4, Jun. 15, 2009.

U.S. Appl. No. 13/158,947, filed Jun. 11, 2011, Zheng, Qian.

U.S. Appl. No. 13/710,536, filed Dec. 11, 2012, Hwang, Cheng S.

U.S. Appl. No. 14/055,037, filed Oct. 16, 2013, Khusial, Permanan Raaj.

U.S. Appl. No. 14/284,869, filed Jun. 15, 2014, Ptchelintsev, Dmitri S.

Avram, "Cellulite: a review of its physiology and treatment," J. Cosmet. Laser Ther. 6: 181-185 (2004).

Bazela et al., "Noninvasive Techniques for Anti-cellulite Product Efficacy Evaluation," Cosmetics and Toiletries magazine vol. 126, No. 5 p. 354-360 (2011).

Bielfeldt et al., "Non-invasive evaluation techniques to quantify the efficacy of cosmetic anti-cellulite products," Skin Research and Technology 14: 336-346 (2008).

Burkill, I.H."A Dictionary of the Economic Products of the Malay Peninsula. vol. II (1-Z)". Ministry of Agriculture and Cooperatives, Kuala Lumpur (1966).

Cleary EG, Gibson MA; Elastin-associated microfibrils and microfibrillar proteins; Int Rev Connect Tissue Res. 1983;10:97-209.

Chopra R. N.,et al.; C. Glossary of Indian Medicinal Plants (Including the Supplement). Council of Scientific and Industrial Research, New Delhi. 1986; Medicinal Plants of Nepal Dept. of Medicinal Plants. Nepal. 1993.

Craft et al., "Relative Solubility, Stability, and Absorptivity of Lutein and Beta-Carotene in Organic Solvents," J. Agric. Food Chem. 40, 431-434 (1992).

Cuervo et al., "Autophagy and Aging: The Importance of Maintaining "Clean" Cells," Autophagy 1(3): 131-140, (2005).

Dickinson et al., "Aminophylline for Cellulite Removal," Pharmacotherapy 30(3): 292-293 (1996).

Gibson MA, et al. "The major antigen of elastin-associated microfibrils is a 31-kDa glycoprotein". J. Bioi. Chern. 261 (24), p. 11429-114236 (1986).

Hexsel et al., "Botanical Extracts Used in the Treatment of Cellulilte," Dermatol. Surg. 31: 866-872 (2005).

Ito et al. Early emphysema in the tight skin and pallid mice: roles of microfibril-associated glycoproteins, collagen, and mechanical forces. American journal of respiratory cell and molecular biology, (Jun. 2006) vol. 34, No. 6, pp. 688-694.

Jiwajinda et al. (2002) Asian Pacific Journal of Cancer Prevention, vol. 3. 215-223.

Kanchanapoom, T. et al.; "Iridoid glucosides from *Thunbergia laurifolia*". Phytochemistry 60:, p. 769-771 (2002).

Kang et al., "Topical N-Acetyl Cysteine and Geinstein Prevent Ultraviolet-Light-Induced Signaling that Leads to Photoaging in Human Skin in vivo," J. Invest. Dermatol. 120:835-841 (2003).

Kligman et al., "Topical retinol improves cellulite," J. Dermatol. Treatment 10: 119-125 (1999).

Lotti et al., "Proteoglycans in So-Called Cellulite," Int. J. Dermatol. 29: 272-274 (1990).

McCullough et al., "Prevention and Treatment of Skin Aging," Ann. N.Y. Acad. Sci. 1067: 323-331 (2006).

Naibaho et al., "Physico-chemical Properties of Plant Extracts from Yanang (*Tiliacora triandra*) Leaves," Agricultural Sci. J. 43(2)(Suppl.) 533-536 (2012).

Nanasombat et al., "Antimicrobial, antioxidant and anticancer activities of Thai local vegetables,"J. Med. Plants Res. vol. 3(5), pp. 443-449 (2009).

Phadungkit, et al., "Phytochemical screening, antioxidant and antimutagenic activities of selected Thai edible plant extracts," J. Medicinal Plants Research vol. 6(5), pp. 662-666 (2012).

Picture of Chinese Ixora, Accessed on Dec. 18, 2012, pp. 1.

Proikas-Cezanne et al. WIPI-1a (WIPI49), a member of the novel 7-bladed WIPI protein family, is aberrantly expressed in human cancer and is linked to starvation-induced authophagy. Oncogene 23(58): 9314-9325, 2004.

Rosenbaum et al., "An Exploratory Investigation of the Morphology and Biochemistry of Cellulite," Plastic and Reconstructive Surgery. vol. 101, Issue 7: 1934-1939 (1998).

Scharffetter-Kochanek et al., "Singlet Oxygen Induces Collagenase Expression in Human Skin Fibroblasts," FEBS vol. 331, No. 3, pp. 304-306 (1993).

Vasudesan, N,V.; Indian Medicinal Plants, vol. IV, Orient Longman Ltd, Chennai, 1995, 172.

Wagenseil JE, Mecham RP; New Insights into Elastic Fiber Assembly; Birth Defects Res C Embryo Today. Dec. 2007; 81(4):229-40.

(56) References Cited

OTHER PUBLICATIONS

Weinbaum JS, et al.; Deficiency in Microfibril-associated Glycoprotein-1 Leads to Complex Phenotypes in Multiple Organ Systems; The Journal of Biological Chemistry, vol. 283, No. 37, Sep. 12, 2008, pp. 25533-25543.

Yang et al., "Lipoic acid prevents high-fat diet-induced dyslipidemia and oxidative stress: A microarray analysis," Nutrition 24: 582-588 (2008).

Bignay, "Fruits of Warm Climates," Euphorbiaceae p. 210-212 (1987).

Faraco et al., RecName: Full=Microfibrillar-associated protein 2; Short=MFAP-2; AltName: Full=Microfibrilassociated glycoprotein 1; Short=MAGP; Short=MAGP-1; Flags: Precursor. GenBank Accession No. P55001. Dec. 15, 2009; p. 1, definition (2009).

Ho et al.. WIPI1 Coordinates Melanogenic Gene Transcription and Melanosome Formation Via TORC1 Inhibition, Journal of Biological Chemistry, vol. 286, No. 14, pp. 12509-12523 (2011).

Keratinocytes—definition of keratinocytes by Medical dictionary, 1 page (2015).

Tiliacora Triandra Fresh 200 Leaves—Milpitas, CA, Manta.com, 20 pages (2015).

\* cited by examiner

A.

B.

USE OF *TILIACORA TRIANDRA* IN COSMETICS AND COMPOSITIONS THEREOF

This application claims priority under 35 U.S.C. §120 as a continuation of application Ser. No. 12/345,707, filed Dec. 30, 2008, the contents of which are hereby incorporated by reference in their entirety.

FIELD

This disclosure generally relates to cosmetic compositions and their use, and more particularly to cosmetic compositions and to their use in improving the condition and appearance of skin.

BACKGROUND

There is an increasing demand in the cosmetics industry to develop products that may be applied topically to the skin that improve the condition and appearance of skin. Consumers are interested in mitigating or delaying the dermatological signs of chronologically- or hormonally-aged skin, as well as skin aging due to the environmental stress, such as fine lines, wrinkles, sagging skin and other conditions due to a progressive loss of cell growth, proliferation and functionality in the epidermal and dermal skin layers. During the aging process, the complexion of the skin, i.e., the color and appearance of the skin, deteriorates slowly from aging and/or exposure to environmental stress, e.g., sunlight. Numerous cosmetic and medical treatments have been developed in an attempt to treat environmentally damaged, aging or aged skin. However, such cosmetics or treatments commonly contain organic acids as their active ingredients or components, and are frequently associated with consumer discomfort, such as burning, itching, and redness.

Therefore, there remains a general need in the cosmetics industry for products that retard or counter the aging effects on the skin, and more specifically for products that produce such effects without undesirable side effects. In particular, there remains a need for topically applied cosmetic compositions that have anti-aging and skin texture benefits using natural plant materials as active components.

Active ingredients or components derived from plants and plant seeds have commonly been employed for a myriad of medicinal, therapeutic and cosmetic purposes. Such actives may be obtained from the entire plant or various parts of a plant, such as seeds, needles, leaves, roots, bark, cones, stems, rhizomes, callus cells, protoplasts, organs and organ systems, and meristems. Active ingredients or components are incorporated in compositions in a variety of forms. Such forms include a pure or semi-pure component, a solid or liquid extract or derivative, or a solid natural plant material. Plant material may be incorporated in a variety of subforms such as whole, minced, ground or crushed, or otherwise physically modified for incorporation into a composition.

*Tiliacora triandra* Diels of the *Tiliacora* family, also known as Yanang, is a species of flowering plant native to mainland Southeast Asia and used particularly in the cuisines of northeast Thailand and Laos. It is a climbing plant with mostly single, smooth, oval-shaped, deep green leaves and yellowish flowers. In traditional Southeast Asian medicine, *Tiliacora triandra* has been used as an herbal medicine for fever relief, alcohol intoxication, inflammation, and bacterial/fungal infection. For instance, the use of *Tiliacora triandra* Diels against *plasmodium falciparum* (cause malaria in humans) is disclosed in Pavanand et al., *Phytother. Res.*, 3, 215-217 (1989).

Safe, effective and new components of compositions to treat, prevent, reduce, inhibit and/or improve the dermatological signs of aging, including environmental stress, due to a progressive degradation of the epidermal and dermal skin layers, would be advantageous for the formulation of treatments and products for the skin. As described herein, novel and beneficial methods and compositions, as well as their mode of action, for the treatment of wrinkles and the like, as well as for personal care products for the skin, are provided herein.

SUMMARY

It is an object of the present disclosure to provide a topical composition having a natural plant material, blends thereof, or components therefrom, in an amount sufficient to prevent, ameliorate and/or reduce dermatological signs of chronologically or hormonally-aged or photo-aged skin, such as fine lines, wrinkles, sagging skin, and other conditions due to a progressive degradation of the skin cell growth, proliferation and functionality in the epidermal and dermal layer, where the plant material, blends thereof or components therefrom are in a cosmetically, dermatologically acceptable vehicle, carrier, or diluent.

It is another object of the present disclosure to provide topical compositions having an extract from at least *Tiliacora triandra* Diels plant, in an amount effective to treat, prevent, control, ameliorate, inhibit, and/or reduce dermatological signs of chronologically or hormonally-aged or photo-aged skin, such as fine lines, wrinkles, sagging skin, and other conditions due to a progressive degradation of the skin cell growth, proliferation and functionality in the epidermal and dermal layer.

Yet another object of the disclosure to provide a topical composition having a natural plant ingredient, which enhances dermal-epidermal cell growth, proliferation and functionality of skin and mechanical properties of skin, as well as, cell-cell cohesion in the epidermis of skin, anchoring of the cells of skin, tissue stability of skin, and communication between cells of skin, in order to improve the aesthetic appearance of skin.

It is still a further object of the present disclosure to provide a method of improving the appearance of skin, including treating the effects of aging in the skin, by topically applying the compositions of the disclosure to the skin.

Further objects, features and advantages of the present disclosure will be better appreciated upon a reading of the detailed description.

These and other objects and advantages of the present disclosure, and equivalents thereof, are achieved by cosmetic compositions having a single natural botanical ingredient or blends of natural botanical ingredients, or components therefrom, and use of such compositions for topical application.

BRIEF DESCRIPTION OF THE FIGURES

FIG. 3A shows lanes 1-5 of the gelatin zymogram: lane 1 is a positive control (10 mM Phenanthroline); lane 2 is a negative control (untreated); and lanes 3-5 are samples treated with 10, 50, and 100 µg/ml of the extract. The reduction in the intensity of the band indicates decrease in enzymatic activity of proteases. FIG. 3B shows measured intensities of each band from FIG. 3A as a percent of the control.

DETAILED DESCRIPTION

Figure 1:
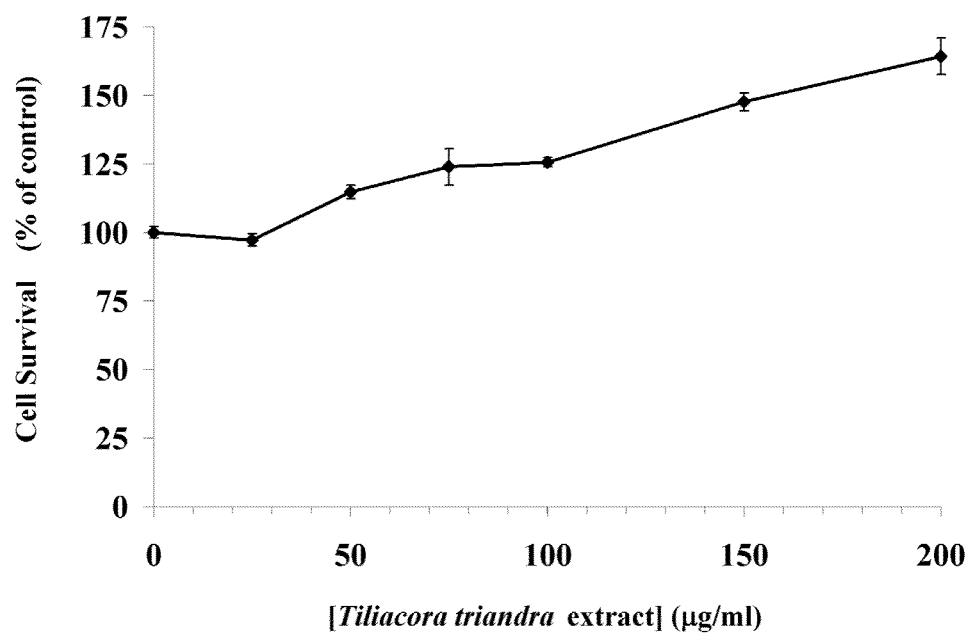
FIG. 1 shows the effect of *Tiliacora triandra* extract on fibroblast cell proliferation/survival. The survival of untreated fibroblast cells (0 µg/ml of extract) was assigned the value of 100%. The survival of treated fibroblast cells at 25, 50, 75, 100, 150, and 200 mg/ml of the extract was determined by comparing the number of treated cells in reference to the untreated cells (control). The standard deviation of each extract concentration is represented by error bars.

The present disclosure provides novel compositions and their methods of use newly found to be effective to treat signs of aging and results relating to the dermatological aging of skin, such as fine lines, wrinkles, sagging skin, and other conditions, due to aging, including chronological aging, hormonal aging and/or photo-aging, to improve the aesthetic appearance of skin. It is to be understood that chronological aging represents the structural, functional, and metabolic changes in the skin that parallel the aging and degenerative change in other body organs, whereas photo-aging is a separate process and largely involves damage to the collagen and elastin fibers in the skin due to an exposure to environment such as the sunlight. Improvements in the aesthetic appearance of the skin may be achieved by topical application of these compositions to the skin on a regular and consistent basis such as daily basis.

It is to be understood that, as used herein, the terms treating and treatment include and encompass reducing, ameliorating, improving, alleviating, and/or eliminating the dermatological effects of aging and/or environmental stress. The present compositions and methods are suitable for use in treating dermatological conditions of the skin in numerous areas of the body, including, without limitation, the face, forehead, lips, neck, arms, hands, legs, knees, feet, chest, back, groin, buttocks, and the like. In a preferred embodiment, the compositions are applied to the face.

One embodiment of the present disclosure relates to the novel use of natural plant materials, such as but not limited to, those from the *Tiliacora* family, or more specifically, the *Tiliacora triandra* Diels plant, or even more specifically, the vines of the *Tiliacora triandra* Diels plant, in a topical composition for application on the face and/or body in order to improve the condition and aesthetic appearance of skin.

Histological studies of the skin show that as aging occurs, the skin undergoes structural, functional, and metabolic changes that parallel the aging and degenerative changes in other body organs. While chronological and/or hormonal aging play a significant role, the number of wrinkles present is also highly dependent on the amount of exposure to environmental stress such as sun exposure due to, in part, oxidative damage from overexposure to ultraviolet (UV) sunlight. As commonly known, the skin is composed of multiple layers of cells, which may be broadly divided into two sections—the top epidermis and the underlying dermis layers.

Epidermis

The epidermis is the topmost layer of the skin that provides waterproofing and serves as a barrier to infection and other external elements. This layer is mostly consists of keratinocyte cells, which originate in the basal layer (the deepest layer of the epidermis) from the division of keratinocyte stem cells. The keratinocytes push up through the layers of the epidermis, undergoing gradual differentiation. While these cells move to the surface of the skin the keratinocytes are enucleated, flattened and highly keratinized. Eventually the keratinocytes die off and form the stratum corneum (the outermost layer of the epidermis), which serves as an effective barrier against the entry of foreign matter and infectious agents into the body and minimizes moisture loss. In normal and healthy skin, keratinocytes are shed and replaced continuously every 30 days. Whereas, in aging skin, the stratum corneum loses its capacity to retain moisture as the rate of keratinocyte renewal is reduced, and the skin dehydrates.

Dermis

The dermis is the underlying layer of the skin located between the epidermis and subcutaneous tissue. It is the thickest of the skin layers and comprises the extracellular matrix of the skin, which is maintained by fibroblast cells. Fibroblasts maintain the structural integrity of connective tissues by continuously secreting precursors of the extracellular matrix. In the aging skin, the fibroblasts which ensure a balance between the synthesis and maturation of both the collagen and elastin fibres, and their breakdown, tip this equilibrium towards the breakdown of collagen and elastin fibres.

In fact, collagen and elastin are the major components in the dermal-epidermal junction (DEJ), i.e., a specialized structures mediating close contact between the lamina densa and the underlying connective tissue of the dermis. The dermal-epidermal junction (DEJ), interlocks forming fingerlike projections called Rete ridges. The cells of the epidermis receive their nutrients and oxygen from the blood vessels in the dermis because the epidermis does not have its own blood vessels. The Rete ridges at the DEJ increase the surface area of the epidermis that is exposed to the dermis, so that the uptake of necessary nutrients/oxygen is more efficient, and the two layers of skin can bind more strongly and resist mechanical stress. The DEJ flattens out with aging, such that the skin is more fragile and more likely to shear. This process also decreases the amount of nutrients/oxygen available to the epidermis by decreasing the surface area in contact with the dermis, thereby interfering with the skin's normal repair process and as a result, the skin shows signs of aging such as fragility, lines and wrinkles, sagging, dull, discoloration, and uneven tone, rough texture, and the like.

Dermis—Collagen

The main structural component of the dermis is a protein called collagen. Bundles of collagen molecules pack together throughout the dermis, accounting for three-fourths of the dry weight of skin. Collagen has great tensile strength, and along with soft keratin, it is responsible for skin strength and elasticity. As aging occurs, the production of collagen is reduced, while the degradation is accelerated due to an overproduction of collagenase, i.e., protease that breaks down collagen. Collagen deficiency may lead to reduction in skin strength and elasticity, which in turn may lead to wrinkles, sagging, and fragility of the aging skin. For a more detailed background on collagen, see Lodish, et al. Molecular Cell Biology, W.H. FREEMAN, New York, N.Y. 4$^{th}$ edition, 2000, the disclosures of which is incorporated herein by reference. Thus, it is anticipated that the retention of or stimulation of collagen production would provide for a healthier and stronger skin, thereby reducing wrinkles, sagging, and fragility of the aging skin.

Thus, the successful restoration of youthful skin from this perspective must address a variety of key issues including: vitality of fibroblasts and keratinocytes, cell-cell adhesion in the epidermis and dermis, cell nourishment to the epidermis, cell-cell anchoring and adhesion between keratinocytes, communication between the dermis and epidermis, collagenase overproduction, collagen replacement, and mechanical properties of the skin. Any natural plant material, including an extract derived therefrom, that addresses these key issues is useful in the topical composition of the present disclosure.

In particular, the natural plant material is, but not limited to, *Tiliacora triandra* Diels, including components or extracts derived therefrom, which stimulates fibroblast and keratinocyte proliferation, increases the expression of collagen, and inhibits collagenase activity, such that when a composition having the natural plant material is administered topically to skin affected by aging or environmental stress, the condition and aesthetic appearance of the skin affected by dermatological signs of aging are improved by lessening facial lines, wrinkles, and sagging skin. The topical composition is preferably applied daily and remains on the affected area.

Topical Composition

As disclosed herein, a topical composition may comprise at least one plant extract in an amount sufficient to stimulate fibroblast and keratinocyte proliferation, increase the expression of collagen, inhibit collagenase activity, or any combination thereof together with a cosmetically, dermatologically, pharmaceutically, or physiologically acceptable vehicle.

The natural plant material may be in any form including, but not limited to, the whole plant, a dried plant, a ground plant, or parts thereof, including but not limited to, seeds, needles, leaves, roots, bark, cones, stems, rhizomes, callus cells, protoplasts, organs and organ systems, and meristems, or components and/or constituents found in, or isolated from, the natural plant material, and/or portions of the plant, or extracts derived either directly or synthetically from the plant, or any combinations thereof. In one embodiment, the natural plant material is in the form of an extract derived from the vines of the natural plant material. It is to be understood that "natural plant material" also includes an ingredient, component, constituent, or extract derived from the natural plant material.

In one embodiment of the disclosure, the topical composition has a plant extract from the *Tiliacora triandra* Diels plant, preferably the vines of the *Tiliacora triandra* Diels plant. However, it is also contemplated that other natural plant materials or blends thereof may work equally well if they stimulate fibroblast and keratinocyte proliferation, increase the expression of collagen, inhibit collagenase activity, or any combination thereof together.

More specifically, this plant material, i.e., the vines of the *Tiliacora triandra* Diels plant, has been newly found to provide treatment for the reduction in signs of dermatological aging by stimulating fibroblast and keratinocyte proliferation, increasing the expression of collagen, and inhibiting collagenase activity. These plant materials have been newly determined to be effective anti-aging or prophylactic agents in compositions and methods for reducing signs of aging. Specifically, the natural plant materials, which increase proliferation of fibroblasts and keratinocytes, cell-cell adhesion in the epidermis and dermis, cell nourishment to the epidermis, cell-cell anchoring and adhesion between keratinocytes, communication between the dermis and epidermis, collagenase overproduction, collagen expression, and mechanical properties of the skin, alleviate the dermatological signs of chronologically or hormonally-aged or photo-aged skin, such as fine lines, wrinkles, and sagging skin, and other conditions due to a progressive degradation of the skin cell growth, proliferation and functionality in the epidermal and dermal layer. The composition comprising these plants are effective when topically applied, preferably in a daily manner. Without wishing to be bound by theory, the natural plant materials, which increase production of collagen; inhibit collagenase activity; and stimulate fibroblast and keratinocyte proliferation, exert their effects by preferably stimulating an increase in anchoring and adhesion between keratinocytes, promoting cell-cell adhesion in the epidermis and dermis, improving cell nourishment to the epidermis, improving communication between the dermis and epidermis, strengthening dermal-epidermal junctions, as well as, cell-to-cell cohesion in the epidermis of skin, anchoring of the cells of skin, and tissue stability of skin. Topical application of the plant compositions also facilitates the targeted delivery of active components without the requirement of an injection or the expertise of a health practitioner.

As disclosed herein, the compositions have a concentration of plant extract of from about 0.0001 wt % to about 90 wt %, about 0.001 wt % to about 25 wt %, about 0.01 wt % to about 10 wt %, and about 0.05 wt % to about 1%, based on the total weight of the composition. One of ordinary skill in the art would be able to adjust the amount of extract used based upon the specific application or effect desired.

The plant component(s) of the present disclosure are preferably contained in a cosmetically or dematologically acceptable vehicle, medium, diluent or carrier. In an embodiment embracing topical application, the compositions of this disclosure comprise a medium (vehicle, diluent or carrier) that is compatible with human skin. The compositions can be formulated as aqueous, alcohol, or aqueous/alcohol-based solutions, ointments, lotions, gels, water-in-oil, oil-in-water, of water-oil-water triple emulsions having the appearance of a cream or gel, microemulsions, or aerosols. In addition, the compositions can be in the form of vesicular dispersions containing ionic and/or nonionic lipids, as described above. Dosage units suitable for such compositions are formulated according to the conventional knowledge and techniques used in the art.

Methods of Using Natural Plant Materials

In one embodiment, the present invention encompasses a method of improving the condition and aesthetic appearance of skin, comprising applying to an affected area of skin, a composition containing a natural plant material of *Tiliacora triandra*, or extract therefrom, in order to increase production of collagen; inhibit collagenase activity; and stimulate fibroblast and keratinocyte proliferation, which exert their effects by preferably stimulating an increase in anchoring and adhesion between keratinocytes, promoting cell-cell adhesion in the epidermis and dermis, improving cell nourishment to the epidermis, improving communication between the dermis and epidermis, strengthening dermal-epidermal junctions, as well as, cell-to-cell cohesion in the epidermis of skin, anchoring of the cells of skin, and tissue stability of skin.

Another embodiment relates to the use of the topical composition as an anti-aging prophylactic agent for improving the condition and aesthetic appearance of skin and comprises applying to the skin, or introducing via a directed mode of delivery, a composition including one or more natural plant materials, or components derived therefrom, in an amount effective to improve the aesthetic appearance of conditions related to skin, where the natural plant material stimulates fibroblast and keratinocyte proliferation, increases production of collagen; inhibits collagenase activity; or a combination therefrom.

In a specific embodiment, the component is in an extract of one or more of the natural plant materials described in a pharmaceutically, physiologically, cosmetically, and dermatologically-acceptable vehicle, diluent, or carrier, where the composition is topically applied to an affected area of skin and left to remain on the affected area in an amount effective for treatment for the dermatological signs of aging and improving the condition and aesthetic appearance of skin.

As will be appreciated by the practitioner, cosmetic treatments comprising compositions containing natural plant materials, including extracts, components, and/or constituents of the invention may be carried out, for example, by topically applying the cosmetic composition as described herein according to the routine technique for administering such compositions. The topical cosmetic composition preferably is applied once daily for a period of at least one week, but may include a period of about 2, 4, 8, or 12 weeks. The cosmetic composition is preferably applied to the face and neck, but may be applied to any area of skin in need of aesthetic improvement, where the cosmetic composition remains on the affected area of skin, and preferably not removed or rinsed off the skin. Routine and commonly practiced techniques encompass the application of creams, lotions, gels, masks, sera, ointments, patches, makeup, makeup-removing milks, sunscreen compositions, or the like, to the skin. Preferably the cosmetic composition is a topical leave on formulation, where spraying as a form of application is also envisioned.

In a particular embodiment of the invention, the topical compositions having a natural plant material such as but not limited to, *Tiliacora triandra*, including components or extracts derived therefrom, are useful for improving the condition and aesthetic appearance of skin affected by aging, particularly matured or maturing skin, by anyone of the following methods: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; ameliorating the effects of estrogen imbalance; preventing and/or treating skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation; and any combinations thereof.

The active components of the disclosed topical composition are further useful in treating, preventing, arresting, ameliorating, reducing or diminishing medical and/or dermatological conditions of skin affected by aging. Such conditions, as used herein, commonly include, but are not limited to, dermatological aging (chronological aging, hormonal aging and/or actinic aging), dermatitis, skin and hair fragility, hirsutism, rosacea, skin blemishes, sensitive skin, hyperpigmentation or hypopigmentation, thinning skin, roughness, keratosis, skin atrophy, wrinkles, lines, hyperplasia, fibrosis, and any combinations thereof. The active components of the topical composition may also be useful in enhancing the general health, vitality, condition, and appearance of the skin.

Gene expression may be measured by the determination of RNA levels in cultured cells, for example, using techniques such as Northern blot technology and the polymerase chain reaction (PCR), e.g., "real time" PCR and reverse transcription PCR (RT PCR) as practiced in the art. (see, e.g., Sambrook et al., 1989, *Molecular Cloning: A Laboratory Manual*, Cold Spring Harbor Laboratory, Cold Spring Harbor, N.Y.; R. Higuchi et al., 1992, *Biotechnology*, 10:413-417; R. Higuchi et al., 1993, *Biotechnology*, 11: 1026-1030; E. S. Kawasaki, 1990, "Amplification of RNA", In: *RNA Protocols: A Guide to Methods & Applications*, M. A. Innis et al., Academic Press, San Diego, Calif., pp. 21-27; all of which are herein incorporated by reference). In addition, gene expression in skin, skin substitute, or cultured cells may be evaluated using gene (cDNA) arrays (microarrays or nucleic acid genechip test arrays comprising membrane, glass, plastic or silicon support materials or the like), serial analysis of gene expression (SAGE), (e.g., as described by V. E. Velculescu et al., *Science*, 270(5235):484-487, 1995; A. Lal et al., *Cancer Res.*, 59(21):5403-5407, 1999; both of which are herein incorporated by reference), or differential display techniques all of which are commonly known and used in the art.

The topical compositions use plant materials/active ingredients affected by genes associated with dermatological signs of aging, such as fine lines, wrinkles, and sagging skin as a biomarker for compounds which may improve the condition and appearance of affected skin. If expression levels of such nucleic acid/protein biomarkers are modified or elevated in the presence of a natural plant material or active ingredient therefrom, the natural plant material may be used in a topical composition of the invention for improving the condition and appearance of skin. Such expression level assays embrace a variety of methods for measuring nucleic acid levels in cells that have been exposed to one or more test substances. Suitable methods include detection and evaluation of gene activation or expression of, for example, DNA, RNA, or mRNA. As non limiting examples, polymerase chain reaction (PCR) assays (e.g., RT-PCR), Northern blotting, in situ hybridization, and other assays as known and practiced in the art may be employed to quantify RNA in cells being assayed for tolerance to a particular treatment (see, e.g., J. O'Connell, 2002, *RT-PCR Protocols*, Humana Press, Totowa, N.J.; R. Rapley and D. L. Manning, 1998, *RNA Isolation and Characterization Protocols*, Humana Press; R. Rapley, 2000, *Nucleic Acid Protocols Handbook*, Humana Press; all of which are herein incorporated by reference). In accordance with such assays, if levels of at least one nucleic acid biomarker are elevated in the presence of one or more test substances, this may predict that the substance(s) will improve the dermatological signs of aging. These substances, or natural plant materials, may then be used in a topical composition, preferably applied daily to the skin, in order to treat, prevent, ameliorate, and/or reduce, signs of dermatological aging, especially fine lines, wrinkles, and sagging skin, thereby improving the condition and aesthetic appearance of skin.

In another embodiment, the plant extract as used herein, also includes "synthetic" extracts, i.e., various combinations of known plant components and/or constituents that are combined to substantially mimic the composition and/or activity of a plant extract of natural origin. Such synthetic extracts are included in the term "plant extract". The synthetic extracts will have two or more, three or more, or four or more active ingredients in common with a plant. Most preferably, the synthetic extracts will have substantially the same number of active ingredients as a natural extract. The correspondence of the numerical incidence of active ingredients between the synthetic extracts and the plant or a natural extract may also be described in terms of "percent commonality". Preferably, the synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract. The plant or natural extract for comparison is derived, for example, from the *Tiliacora triandra* plant.

For use in the compositions of this disclosure, the plant or components and/or active constituents are preferably derived directly from the plant. The components may be in a pure form, a semi-pure form, or unpurified form. In one embodiment, the components are in the form of an extract obtained by organic solvent extraction (See Example 1).

Briefly, the organic solvent extraction method involves washing and extracting the plant material using an organic solvent. Non-limiting examples of organic solvents include methanol, ethanol, isopropanol, dichloromethane, chloroform, hexane, xylene, and petroleum ether. Well-known methods in the art may be used for organic solvent extraction.

Organic solvent extraction involves collecting the raw materials from the plant that contain the desired constituent(s), such as seeds, needles, leaves, roots, bark, cones, stems, rhizomes, callus cells, protoplasts, organs and organ systems, and meristems. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time adapted to remove the plant constituents is suitable, with between about 1-8 hours typical, more preferably is between about 2-6 hours, and most preferably is between about 3-5 hours. The temperature of extraction is between about 30° C.-about 90° C., between about 40° C.-about 70° C., and between about 50° C.-about 60° C. The collected extract is then fine-filtered to remove debris, and may be used directly, or is concentrated, for example by distilling the solvent or by other conventional processing, and the extract can also be provided in powder form.

Similarly, aqueous-organic solvent extraction involves initially collecting raw materials from a plant containing the desired alkaloid(s), such as seeds, needles, leaves, roots, bark, cones, stems, rhizomes, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. The Alternatively, organic solvent may then be added to the neutralized solution to transfer the extract actives from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Different plants containing different constituents may be mixed and extracted together. This process of mixed extraction may preferably be used for extracting those plants containing constituents having similar solubility in the solvent used for extraction, such as ethanol. The mixture of extracts may be concentrated and stored in an appropriate solvent.

In one embodiment, the extract may be obtained from the vine of the *Tiliacora triandra* plants. In a preferred embodiment, the extracts may be obtained by drying the plant material and subsequently extracting from the dried plant using a solvent. In one embodiment, a polar solvent may be used. Suitable polar solvents include, but are not limited to, water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); organic acids including acetic acid, and the like; dimethyl sulfoxide; acetonitrile; other organic solvents; and combinations thereof. Other suitable solvents include physiological saline, phosphoric acid buffer and phosphate buffer saline and the like.

Preferably, the *Tiliacora triandra* extract is obtained by extracting *Tiliacora triandra* vine with water, ethanol, or a mixture thereof. The preferred solvent systems will comprise from about 10% by volume to about 90% by volume of ethanol and from about 10% by volume to about 90% by volume of water. More typically, the solvent system will comprise from about 25% by volume to about 75% by volume of ethanol and from about 25% by volume to about 75% by volume of water. Particularly good results are obtained with a solvent system comprising from about 45% by volume to about 55% by volume of ethanol and from about 45% by volume to about 55% by volume of water, with a 50:50 mixture (by volume) of ethanol and water being preferred.

Suitable extraction processes are disclosed in PCT Publications WO03/079816 (describes a process for the preparation of tomato extracts with high content in lycopene), WO04/014404 (describes a process for the preparation of an *Echinacea angustifolia* extract) and WO04/014958 (describes extracting a polysaccharide of *Echinacea angustifolia* roots), all of which are herein incorporated by reference in their entirety.

Application of Natural Plant Materials

The compositions of the present disclosure yield improvements to the aesthetic appearance of the skin by treating dermatological aging, especially chronological, actinic or hormonal aging. In particular, improvements to the aesthetic appearance of skin include at least one of the following: improvement in skin tone, radiance, clarity and/or tautness; improvement in skin firmness, plumpness, suppleness, and/or softness; improvement in skin texture and/or promotion of skin retexturization; improvement in appearance of skin contours, hollow cheeks, sunken eyes, restoration of skin luster and/or brightness; replenishment of essential nutrients and/or constituents in the skin decreased by aging and/or menopause; increase in cell proliferation and/or multiplication; increase in cell metabolism decreased by aging and/or menopause; improvement in skin moisturization; enhancement of skin thickness; reducing skin sensitivity; and an increase in skin elasticity and/or resiliency. By increasing the amount of subcutaneous fat, the extracts of the disclosure may also treat, prevent, reduce, ameliorate, and/or eliminate aesthetically displeasing wrinkles, frown lines, hallow cheeks, sunken eyes, fine lines, folds, furrows, or neck bands, etc. that can arise from aging.

In accordance with this disclosure, the components from the plants comprise compositions which include, without limitation, topically applied formulations, anti-oxidants, anti-inflammatories, sunscreens, cosmetics, including make-ups, anti-aging formulations, e.g., creams for fine lines and/or wrinkles, topicals, skin penetration enhancers, sprays, and the like. Also in accordance with this disclosure, the plant components and additional ingredients comprising such compositions can be formulated in a variety of product forms. Preferably, the compositions are prepared in targeted delivery systems, e.g. creams, lotions, gels, serums, transdermal patches, and the like, particularly for topical administration. Targeted delivery and/or penetration enhancement may also be achieved by iontophoresis.

The present disclosure further provides the compositions comprising the plant components preferably for topical administration or for targeted delivery without inducing significant irritation. Thus, the inventive compositions are especially suitable for sensitive skin. The compositions are applied to the skin for a period of time sufficient to improve the aesthetic appearance of skin. The compositions are preferably applied topically once, twice, or more daily, preferably, once daily. The daily application is preferably for a period of one week, two weeks, four weeks, or more. The compositions can be formulated into liposomes which can comprise other additives or substances, and/or which can be modified to more specifically reach or remain at a site following administration.

The present disclosure encompasses compositions comprising a cosmetically or dermatologically acceptable formulation which is suitable for contact with living animal tissue, including human tissue, with virtually no adverse physiological effect to the user. Compositions embraced by this disclosure can be provided in any cosmetically and/or dermatologically suitable form, preferably as a lotion or cream, but also in an anhydrous or aqueous base, as well as in a sprayable liquid form. Other suitable cosmetic product forms for the compositions of this disclosure include, for example, an emulsion, a lip balm, a lip gloss, a lotion, a mask, an ointment, a mousse, a patch, a pomade, a solution, a spray, a wax-based stick, or a towelette. In addition, the compositions contemplated by this disclosure can include one or more compatible cosmetically acceptable adjuvants commonly used and known by the skilled practitioner, such as colorants, fragrances, emollients, humectants, preservatives, vitamins, chelators, thickeners, anesthetics, anti-allergenics, antifungals, antimicrobials, other anti-inflammatory agents, antioxidants, antiseptics, depigmenting agents, film formers, insect repellents, pharmaceutical agents, photostabilizing agents, sunscreens, stabilizers, surfactants, thickeners, viscosity modifiers, and the like, as well as other botanicals such as aloe, chamomile, and the like, and as further described below.

Cosmetically or dermatologically acceptable vehicles that can be used in the present topical compositions include, but are not limited to, one or more aqueous systems, glycerins, C1-4 alcohols, fatty alcohols, fatty ethers, fatty esters, polyols, glycols, vegetable oils, mineral oils, liposomes, laminar lipid materials, silicone oils, water or any combinations thereof.

In the present disclosure, the vehicle may be in the form of an aqueous phase, an oil phase, a gel, a wax-in-water emulsion, a silicone-in-water emulsion, a water-in-silicone, an oil-in-water emulsion, or a water-in-oil emulsion. The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate product form, the ingredients contained therein, as well as the method for preparing it, on the basis of the knowledge that the skilled artisan possesses.

The composition may include an aqueous phase which may contain water or a mixture of water and at least one hydrophilic organic solvent such as an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 to about 99.99 wt % by weight of the composition.

When the composition of the disclosure is in the form of an emulsion, it can also optionally comprise a surfactant, preferably in an amount of from 0.1 to 30% and in particular from about 1 to about 20 wt % by weight of the composition.

The composition can also comprise a thickening polymer such as an amphiphilic polyurethane, a polyacrylic homopolymer or copolymer, a polyester, and/or a hydrocarbon-based resin. The polymers can be dissolved or dispersed in the cosmetically acceptable vehicle and optionally combined with a plasticizer.

The composition of the disclosure may also comprise an oil phase containing oil soluble or oil dispersible ingredients that are liquid at room temperature (25° C.) and/or oily or waxy substances that are solid at room temperature, such as waxes, semisolids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polymethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of 0 wt % to about 90 wt %, preferably from about 1 wt % to 80 wt % by weight of the oil phase.

The oil phase of the composition of the disclosure may also comprise one or more cosmetically acceptable organic solvents. These solvents are present in an amount of 0 wt % to about 60 wt %, preferably about 1 wt % to 30 wt % by weight of the composition and can be selected from the group consisting of lipophilic organic solvents, amphiphilic organic solvents and mixtures thereof. Suitable solvents which can be used in the composition of the disclosure include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the disclosure may further comprise any ingredient conventionally used in the cosmetic field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetic field to achieve their intended purpose, and range typically from about 0.01 wt % to about 20 wt % by weight of the composition. The nature of these ingredients and their amounts must be compatible with the production of the compositions of the disclosure.

The composition of the disclosure may also comprise an additional particulate phase, typically present in an amount of 0 wt % to about 30 wt % by weight of the composition, preferably from about 0.05 wt % to about 20 wt %, and which can comprise pigments and/or pearlescent agents and/or fillers used in cosmetic compositions. Suitable inorganic pigments include titanium oxide, zirconium oxide and cerium oxide, as well as zinc oxide, iron oxide, chromium oxide and ferric blue. Suitable organic pigments include barium, strontium, calcium, and aluminium lakes and carbon black Suitable pearlescent agents include mica coated with titanium oxide, with iron oxide, or with natural pigment. Fillers are normally present in an amount of 0 to about 20 wt. % by weight of the composition, preferably about 0.1 to about 10 wt %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Corning), and silicone resin microbeads (Tospearl from Toshiba).

The oil phase of the compositions of the disclosure may comprise one or more waxes, gums, or mixtures thereof. The waxes include hydrocarbon-based waxes, fluoro waxes and/or silicone waxes and can be of plant, mineral, animal and/or synthetic origin. In particular, the waxes have a melting point of greater than 25° C., preferably greater than 45° C. The compositions of the present disclosure may contain from 0 to about 20 wt % waxes by weight of the composition. The gums are generally high molecular weight PDMSs or cellulose gums or polysaccharides and the semisolid materials are generally hydrocarbon-based compounds such as lanolins and derivatives thereof or alternatively PDMSs. The compositions of the present disclosure may contain from 0 to about 20 wt % gums by weight of the composition, typically from about 0.1% wt to about 10 wt %.

Also, embraced by the present disclosure are transdermal modes of delivery, such as patches and the like, with or without a suitable penetration enhancers. The methods and compositions embodied by the disclosure provide a means by which the components can be effectively administered in a transdermal system. Accordingly, a transdermal means of delivering a composition or formulation (often with a penetration enhancing composition) to the skin is that of the transdermal patch or a similar device as known and described in the art. Examples of such devices are disclosed in U.S. Pat. Nos. 5,146,846; 5,223,262; 4,820,724; 4,379,454 and 4,956,171; such descriptions are not meant to be limiting. The transdermal mode of storing and delivering the compositions onto the skin and forming the active composition is convenient and well suited for the purposes of an embodiment of the present disclosure. In a preferred method, the application is through a sustained release vehicle, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

Another particular embodiment of the present disclosure is directed to the delivery of the described compositions by the use of targeted delivery systems, for example, liposomes, microspheres (see, e.g., U.S. Pat. No. 5,770,222 to Unger et al.), and the like, so that the components and/or active constituents can more readily reach and affect the subcutaneous layer of the area of application, e.g., face or neck, or the other area of the skin.

In another preferred embodiment, the topical compositions of the present disclosure also include at least one of the following: a skin penetration enhancer, a surface smoother, a skin plumper, an optical diffuser, a sunscreen, an exfoliation promoter, and an antioxidant. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety.

A surface smoother provides the functional benefits of enhancing skin smoothness and reducing the appearance of fine lines and coarse wrinkles. Examples include isopropyl myristate, petrolatum, isopropyl lanolate, silicones (e.g., methicone, dimethicone), or any mixtures thereof. The surface smoother is preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present disclosure include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt % of the total weight of the composition.

A sunscreen protects the skin from damaging ultraviolet rays. In an illustrative embodiment of the present disclosure, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt % of the total weight of the composition. The addition of a sunscreen may prevent/reduce the photodegradation of the composition while in the package as well as serve to protect the skin from ultraviolet radiation.

The compositions of the present disclosure having sunscreen bring about additional improvements to the aesthetic appearance of skin, including at least one of the following: minimizes sunburning, minimizes tanning, and reduces redness.

The present compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof.

When the present disclosure includes an exfoliation promoter, the composition has about 0.5 wt % to about 30 wt %, preferably about 1 wt % to about 15 wt %, more preferably about 4 wt % to about 10 wt %, and most preferably about 4 wt %, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/ esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present disclosure may have an antioxidant preferably from about 0.001 wt % to about 10 wt %, and more preferably from about 0.001 wt % to about 5 wt %, of the total weight of the composition.

The present composition may also have one or more of the following active agents, ingredients or adjuvants: anesthetics, anti-allergenics, antifungals, antiseptics, chelating agents, colorants, demulcents, emollients, emulsifiers, fragrances, humectants, lubricants, moisturizers, pH adjusters, pigment altering agents, preservatives, stabilizers, surfactants, thickeners, viscosity modifiers, vitamins, or any mixtures thereof. The amounts of these various substances are those that are conventionally used in the cosmetic or pharmaceutical fields, for example, they can constitute from about 0.01% to about 20% of the total weight of the composition.

Non limiting examples of active agents for formulating into the compositions of the present disclosure include those reagents having an effect on the treatment of wrinkles and/or fine lines, in addition to the natural plant actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to about 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

More particularly, the compositions for topical application can be in the form of a protective care composition for the skin, preferably for the face, the neck, the hands, the feet, or other areas of the body. Non-limiting examples include day creams or lotions, night creams or lotions, sunscreen creams, lotions, or oils, body milks, makeup (a foundation), artificial tanning compositions, depilatories, and patches.

Emulsifiers are typically present in emulsion compositions of the disclosure in an amount of about 0.1% to about 30%, by weight and preferably from about 0.5% to about 30% by weight relative to the total weight of the composition. However, not all compositions will necessarily include emulsifiers.

EXAMPLES

The following examples describe specific aspects of the disclosure to illustrate the disclosure and provide a description of the present methods for those of skill in the art. The examples should not be construed as limiting the disclosure, as the examples merely provide specific methodology useful in the understanding and practice of the disclosure and its various aspects.

Example 1

The plant of the present disclosure can be extracted from natural raw materials by using methods of aqueous-organic solvent extraction as is well known in the art. Two such extraction processes are set forth below.

Extraction of *Tiliacora triandra* by Ethanol

An extract was obtained by extracting the vine of the *Tiliacora triandra* plant using an ethanol extraction scheme. Briefly, the vines of *Tiliacora triandra* Diels were first manually ground into small particles resulting in a powder of about 250 grams per flask (2 flasks). The ground powder was then extracted with 80% ethanol (2×2,000 ml per flask). After filtering and vacuum evaporation, the total concentrated extract was lyophilized resulting in an ethanolic extract of 50 grams. Tannins were removed resulting in an ethanolic extract of *Tiliacora triandra* of 46.04 grams.

Extraction of *Tiliacora triandra* by Hexane

An extract was obtained by extracting the vine of the *Tiliacora triandra* plant using a hexane extraction scheme. Briefly, the vines of the *Tiliacora triandra* were first manually ground into small particles resulting in a powder of about 250 grams per flask (2 flasks). The ground powder was then extracted with 100% hexane (2×2,000 ml per flask). After filtering and vacuum evaporation, the total concentrated extract was dried by hot air oven at 40 C resulting in an hexanolic extract of *Tiliacora triandra* of 0.61 grams.

Example 2

Cell Proliferation/Cytotoxicity Assay

Keratinocyte and fibroblast cells were plated in 96 well plates (1.0×104 cells/well) with 100 μL culture medium with growth supplements (e.g., Epilife medium from Cascade Biologics Inc.). The plated cells were incubated at 37 C for 24 hours. After 24 hours, various concentrations of plant extract of Example 1 were added to each well and incubated for another 48 hours. The metabolic activity or cell viability of each treated well was determined by the MTT (3-(4,5-dimethylthiazol-2-yl)-2,5-diphenyltetrazolium bromide) assay in reference to the untreated cells. After removal of 100 μL medium, MTT stock dye solution was added (15 μL/100 μL medium) to each well and incubated at 37 C in 5% $CO_2$ atmosphere for 4 hours. If the cell was viable, the pale yellow MTT was converted into a dark blue formazan crystals and accumulated within that cell. After 4 hours, the solubilization solution (100 μL) was added to each well, mixed thoroughly to dissolve the insoluble formazan crystals. Since, the number of surviving cells is directly proportional to the level of the formazan product created, the absorbance was measured by using ELISA plate reader at 540 nm with a reference wavelength of 630 nm to determine cell viability (survival). The cell survival data of fibroblasts and keratinocytes are plotted as percent (%) cell survival versus control untreated cells in FIGS. 1 & 2.

Figure 2:
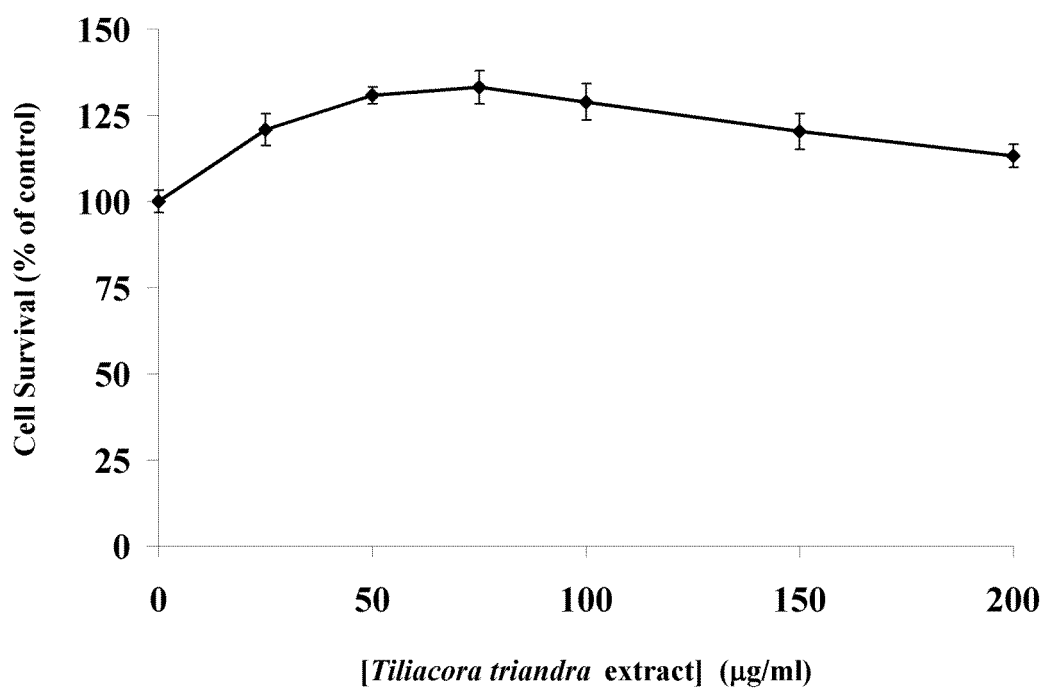
FIG. 2 shows the effect of *Tiliacora triandra* extract on keratinocyte cell proliferation/survival. The survival of untreated keratinocyte cells (0 µg/ml of extract) was assigned the value of 100%. The survival of treated keratinocyte cells at 25, 50, 75, 100, 150, and 200 mg/ml of the extract was determined by comparing the number of treated cells in reference to the untreated cells (control). The standard deviation of each extract concentration is represented by error bars.

FIGS. 1 & 2 show the effects of various concentrations of the *Tiliacora triandra* extract on fibroblast and keratinocyte cell survival, respectively. FIG. 1 shows that the addition of the extract continuously enhances fibroblast survival by more than 50%, whereas, FIG. 2 shows that the addition of the extract enhances keratinocyte survival by as much as 30% at approximately 70 μg/ml of the extract.

Example 3

Assay of Collagen Breakdown

Gelatin Zymography for Analysis of Proteinases

Normal human fibroblast cells were cultured in six well plates. For the assays, cells were cultured at densities of 1×10⁵ cells per well in 2 ml of growth medium. Confluent cells were treated for 24 hours with or without plant extracts in the growth medium. The fibroblast supernatants were subjected to substrate gel electrophoresis in 10% polyacrylamide gels impregnated with 1 mg/ml gelatin. Samples of cell supernatants (0.5 microgram of protein) were mixed with an equal volume of non-reducing Laemmli sample buffer (2% SDS; 125 mM Tris-HCl, pH 6.8, 10% glycerol and 0.001% bromophenol blue) and then electrophoresed. Afterwards, electrophoresis gels were washed twice in 2% Triton X-100 for 20 minutes at room temperature and incubated at 37 C for 16 h in 50 mM Tris-HCl buffer, pH 7.4 containing 5 mM $CaCl_2$. Following incubation, the gels were stained with 0.05% Coomassie Brilliant Blue G-250.

In order to examine the effect of plant extract of Example 1 on enzyme activity, fibroblast supernatants collected above were loaded on preparative gelatin-containing polyacrylamide gels. After electrophoresis the gels were cut in strips of 1 cm, and each strip was incubated at 37 C for 16 h in Tris-$CaCl_2$ buffer containing various concentrations of claimed extract from Example 1. The 1,10-phenantroline compound at 10 mM was used as a control inhibitor. The gels were then extensively washed in 2% Triton X-100 and reincubated in Tris-$CaCl_2$ solution for 16 h at 37 C. In order to quantify the relative inhibition of MMPs by claimed extract, electrophoretic bands were scanned and analyzed by comparing the activity of MMPs with control reactions, where the plant fractions were not included.

Figure 3:
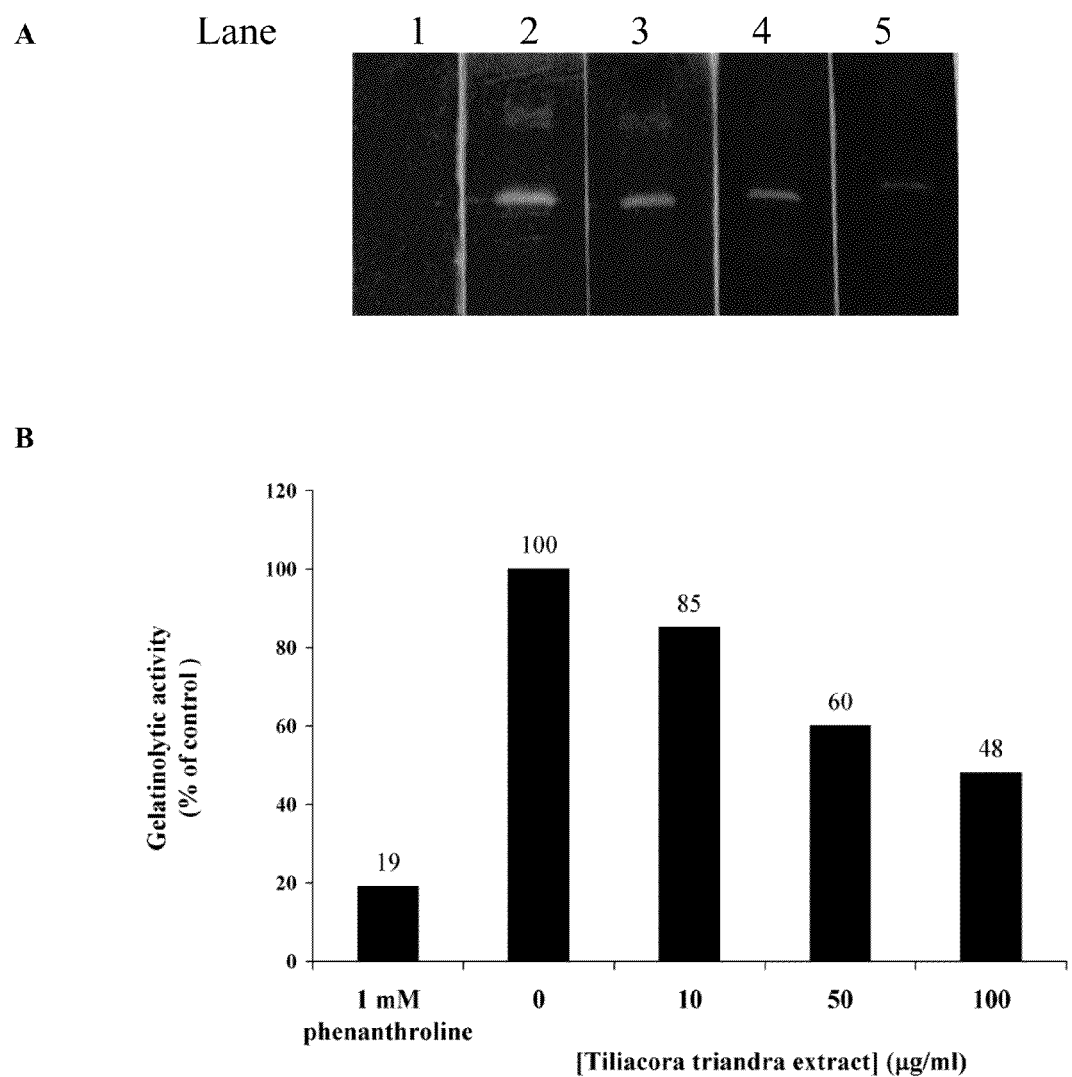
FIG. 3 shows the effect of *Tiliacora triandra* extract on gelatinolytic activity.

FIG. 3 shows the effects of various concentrations of the *Tiliacora triandra* extract on gelatinolytic activity (bands 3 to 5). Gelatinolytic activity was detected as unstained bands. The figure shows that the addition of the extract continuously reduces gelatinolytic activity, which indicates reduction in collagen breakdown due to the *Tiliacora triandra* extract.

Example 4

Assay of Collagen Breakdown

Fluorometric Analysis of Collagenase

Figure 4:
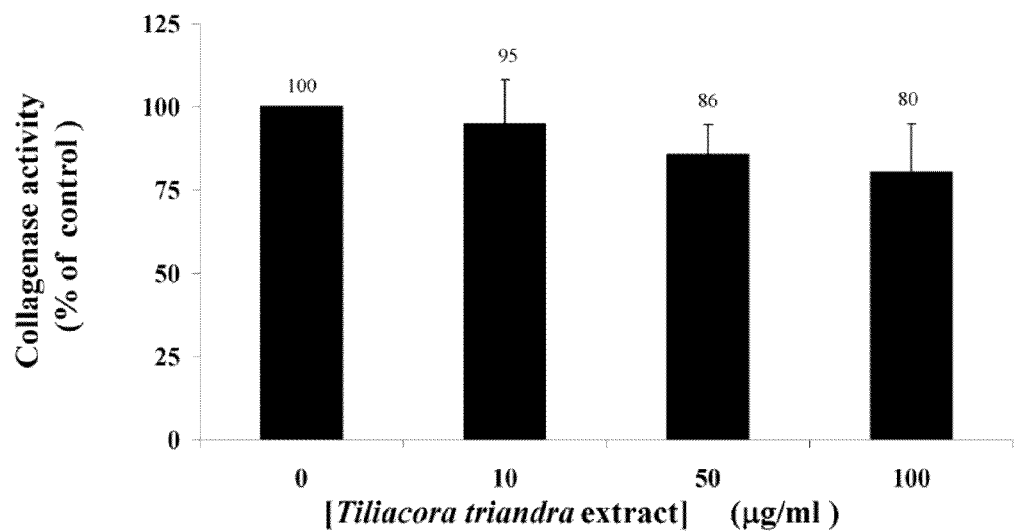
FIG. 4 shows fluorometric analysis of collagenase activity by measuring the digested product of the DQ gelatin (fluorescein labeled gelatin conjugate). The control (untreated) sample is assigned value of 100%. The standard deviation of each extract concentration is represented by error bars.
Figure 4:
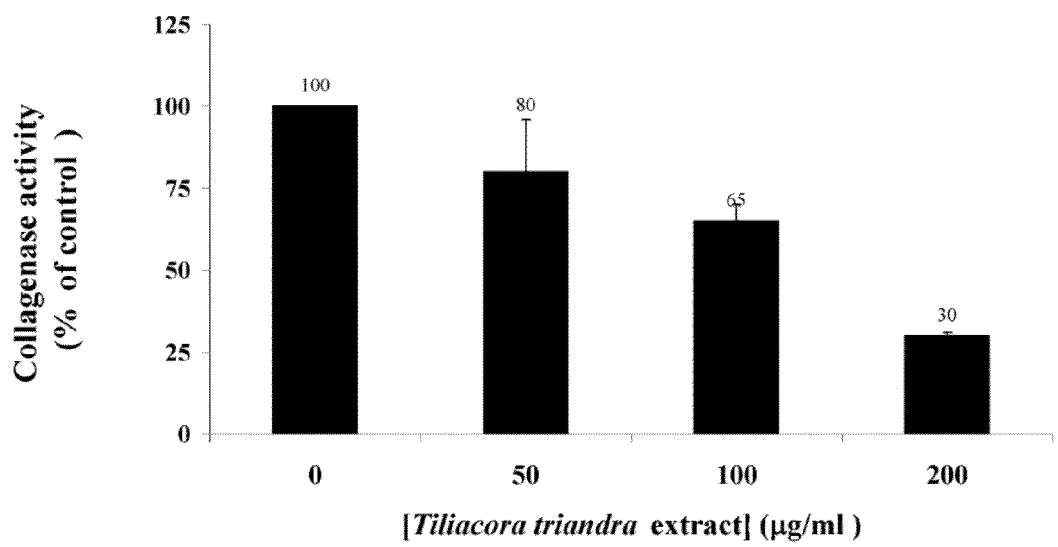

Each assay well was prepared by adding 20 μl of DQ gelatin stock solution to give a concentration of 12.5 μg/ml. The Extract from Example 1 was diluted in 1× Reaction buffer and afterwards *Clostridium* collagenase type III was diluted in 1× Reaction buffer to 0.3 units/ml. 100 μl of the diluted enzyme or 100 μl of 1× Reaction buffer was added as a blank, to the sample wells preloaded with substrate and an aliquot of *Tiliacora triandra* extract. The samples were incubated at 37 C in dark place for 1-30 minutes. Because the reaction is continuous (not terminated), fluorescence intensity was measured at every 1.5 min interval using a conventional spectrofluorometer. Digested products from the DQ gelatin substrates indicates collagenase activity and had absorption maxima at 485 nm and fluorescence emission maxima at 528 nm, FIG. 4A shows the effects of various concentrations of the *Tiliacora triandra* extract on gelatinolytic activity from untreated to treated with 100 μg/ml of the extract. FIG. 4B similarly to FIG. 4A shows the effects of the *Tiliacora triandra* extract on gelatinolytic activity at higher concentrations of the extract, i.e., up to 200 μg/ml. The figures show that the addition of the extract continuously reduces collagenase activity.

Example 5

Survey to Determine Aesthetic Improvement of the Skin

A prototype disclosed in Table 1 are illustrative of a topical composition containing an extract from the vines of the *Tiliacora triandra* plant disclosed in Example 1. The compositions may be tested on multiple subjects (panellists) and compared, for instance, to a commercially available topical compositions. As will be appreciated by the practitioner, panellists can be asked to apply the control composition and a prototype to their skin over a period of hours, days, or months, and evaluate the formulations based on a questionnaire. For instance, panellists may be asked whether the prototype reduces fine lines, wrinkles, sagging skin, and other conditions due to a progressive degradation of the skin cell growth, proliferation and functionality in the epidermal and dermal layer. The results demonstrate the improvement of the aesthetic appearance of aging skin in need thereof due to an application of the prototype.

TABLE 1

Topical compositions containing an extract from the vine of the *Tiliacora triandra* plant.

| Description | Purpose | % Ingredients | | | |
|---|---|---|---|---|---|
| | | Formula 1 | Formula 2 | Formula 3 | Formula 4 |
| Deionized water | diluent | QS | QS | QS | # |
| Acrylates/C10-30 Alkyl Acrylate Crosspolymer | emulsifier | 1 | 1 | 1 | 1 |
| Cetyl Ethylhexanoate | emollient | 10 | 10 | 10 | 10 |
| C12-15 Alkyl Benzoate | emollient | 3.9 | 3.9 | 3.9 | 3.9 |
| Isopropyl Isostearate | emollient | 3 | 3 | 3 | 3 |
| Diisopropyl dimer dillinoleate | emollient | 0.1 | 0.1 | 0.1 | 0.1 |
| Tocopheryl acetate | antioxidant | 0.5 | 0.5 | 0.5 | 0.5 |
| Butylene glycol | humectant | 2 | 2 | 2 | 2 |
| Propylene glycol | humectant | 1 | 1 | 1 | 1 |
| Dimethicone PEG-7 isostearate | co-emulsifier | 0.5 | 0.5 | 0.5 | 0.5 |
| methyl gluceth-20 | humectant | 0.5 | 0.5 | 0.5 | 0.5 |
| Triethanolamine | neutralizer | 1 | 1 | 1 | 1 |
| Acrylates/acrylamide copolymer/mineral oil | emulsifier | 1.5 | 1.5 | 1.5 | 1.5 |
| DMDM Hydantoin/ Iodopropynylbutylcarbonate | preservative | 0.4 | 0.4 | 0.4 | 0.4 |
| *Tiliacora triandra* | botanical extract | 0.2 | 0.1 | 0.01 | 0.01 |

The contents of all patents, patent applications, published articles, abstracts, books, reference manuals and abstracts, as cited herein are hereby incorporated by reference in their entireties to more fully describe the state of the art to which the disclosure pertains.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings.

The invention claimed is:

1. A method of treating wrinkles and/or fine lines by increasing the proliferation of fibroblasts and keratinocytes in skin, comprising topically applying to skin having wrinkles and/or fine lines a topical composition comprising (a) a water and ethanol extract from a vine of the *Tiliacora triandra* Diels plant; and (b) a cosmetically, dermatologically, pharmaceutically, or physiologically acceptable vehicle; wherein the extract is obtained by extraction with a solvent mixture comprising from about 10% by volume to about 90% by volume ethanol and from about 10% to about 90% by volume water; and such that proliferation of fibroblasts and keratinocytes in said skin is increased.

2. The method according to claim 1, wherein the skin is sensitive skin.

3. The method according to claim 1, wherein the composition is topically applied at least once daily for at least one week.

4. The method according to claim 1, wherein the extract is present in an amount about 0.0001 wt % to about 90 wt % based on the total weight of the composition.

5. The method according to claim 4, wherein the extract is present in an amount of from about 0.01 wt % to about 10 wt % of the total weight of the composition.

* * * * *